United States Patent
Wang et al.

(10) Patent No.: US 11,977,679 B1
(45) Date of Patent: May 7, 2024

(54) VR REHABILITATION TRAINING METHOD AND SYSTEM WITH QUANTITATIVE EVALUATION FUNCTION

(71) Applicant: Shenzhen Yiwei Medical Technology Co., Ltd, Shenzhen (CN)

(72) Inventors: Silun Wang, Shenzhen (CN); Chi Zhang, Shenzhen (CN)

(73) Assignee: Shenzhen Yiwei Medical Technology Co., Ltd, Shenzhen (CN)

( * ) Notice: Subject to any disclaimer, the term of this patent is extended or adjusted under 35 U.S.C. 154(b) by 0 days.

(21) Appl. No.: 18/399,809

(22) Filed: Dec. 29, 2023

(30) Foreign Application Priority Data

Feb. 24, 2023 (CN) .......................... 202310159510.2

(51) Int. Cl.
  G06F 3/01 (2006.01)
  G02B 27/00 (2006.01)
  G16H 20/30 (2018.01)
(52) U.S. Cl.
  CPC .............. *G06F 3/013* (2013.01); *G06F 3/012* (2013.01); *G16H 20/30* (2018.01)
(58) Field of Classification Search
  CPC .......... G06F 3/013; G06F 3/012; G16H 20/30
  See application file for complete search history.

(56) References Cited

U.S. PATENT DOCUMENTS

2021/0349528 A1* 11/2021 Son ......................... G06F 3/013

FOREIGN PATENT DOCUMENTS

| CN | 109731292 A | 5/2019 |
| CN | 110947163 A | 4/2020 |
| CN | 112450949 A | 3/2021 |
| CN | 113035413 A | 6/2021 |
| CN | 113591550 A | 11/2021 |

* cited by examiner

*Primary Examiner* — Deeprose Subedi
(74) *Attorney, Agent, or Firm* — Nitin Kaushik

(57) ABSTRACT

An embodiment of the present disclosure discloses a virtual reality (VR) rehabilitation training method with a quantitative evaluation function. The method includes: obtaining attribute information of a user to be trained, and playing short scenarios based on the attribute information; during the playing, acquiring pupil change information and action information of the user in real time, so as to determine a training scenario that the user is interested in and a training solution; generating a virtual training scenario based on the training scenario that the user is interested in; obtaining a head position of the user to be trained, and generating a virtual body model; generating a virtual distractor in the virtual training scenario based on the training solution; and tracking and recording somatosensory signals of the user to be trained at six degrees of freedom, and performing functional quantitative analysis to obtain functional quantitative results.

7 Claims, 7 Drawing Sheets

VR REHABILITATION TRAINING METHOD AND SYSTEM WITH QUANTITATIVE EVALUATION FUNCTION

CROSS-REFERENCE TO RELATED APPLICATIONS

The application claims priority to Chinese patent application No. 2023101595102, filed on Feb. 24, 2023, the entire contents of which are incorporated herein by reference.

TECHNICAL FIELD

The present disclosure relates to the field of data processing technologies, in particular to a VR rehabilitation training method and system with a quantitative evaluation function.

BACKGROUND

The virtual reality (VR) technology is a technology that uses a computer to create a virtual environment (such as walking and object fetching) that simulates real things, and makes an experiencer "put" into the environment through a specific interactive tool such as stereo glasses and sensor gloves, to implement direct natural interaction between the experiencer and the virtual environment. Virtual reality systems can provide users with the same feeling of being protagonists in a simulated environment as in the real world.

In recent years, the virtual reality technology has begun to be applied in rehabilitation training of limb function. Patients are enabled to complete controllable functional movements and operations in a virtual environment to achieve the purpose of functional reconstruction.

The virtual reality technology can not only improve the interestingness of exercise rehabilitation training by creating a virtual environment, but also stimulate and maintain the interest of patients in repeated exercises through feedbacks in various forms.

However, at present, virtual reality is basically that rehabilitation trainees follow virtual games to do some prescribed actions, which is accompanied with two shortcomings: on the one hand, there is no way to provide a quantitative evaluation for rehabilitation training, and on the other hand, the current game scenario is simplex and cannot meet personalized requirements, resulting in a poor effect of current training.

SUMMARY

In view of the problem of a poor training effect, a VR rehabilitation training method and system with a quantitative evaluation function are proposed.

A VR rehabilitation training method with a quantitative evaluation function is proposed in an embodiment of the present disclosure. The method includes:
  obtaining attribute information of a user to be trained, and determining a corresponding evaluation program based on the attribute information, where the attribute information includes a height, a weight, and a gender, and the evaluation program is used for selecting a plurality of short scenario items to play;
  during the playing, acquiring pupil change information and action information of the user in real time, determining a training scenario that the user is interested in based on the pupil change information, and determining a training solution based on the action information of the user;
  generating a virtual training scenario based on the training scenario that the user is interested in;
  obtaining a head position of the user to be trained, generating a virtual body model, and presenting the virtual body model in the virtual training scenario;
  generating a virtual distractor in the virtual training scenario based on the training solution, where the user to be trained controls the virtual body model through motion to change the position to avoid the virtual distractor; and
  tracking and recording somatosensory signals of the user to be trained at six degrees of freedom, and performing functional quantitative analysis based on the somatosensory signals at the six degrees of freedom to obtain functional quantitative results.

A VR rehabilitation training system with a quantitative evaluation function is proposed. The system includes:
  a VR head display main control terminal configured to: obtain attribute information of a user to be trained, and determine a corresponding evaluation program based on the attribute information, where the attribute information includes a height, a weight, and a gender, and the evaluation program is used for selecting a plurality of short scenario items to play; during the playing, acquire pupil change information and action information of the user in real time, determine a training scenario that the user is interested in based on the pupil change information, and determine a training solution based on the action information of the user; and generate a virtual training scenario based on the training scenario that the user is interested in;
  a VR head display somatosensory recognition module configured to obtain a head position of the user to be trained, generate a virtual body model, and present the virtual body model in the virtual training scenario;
  a VR motion interaction module configured to generate a virtual distractor in the virtual training scenario based on the training solution, where the user to be trained controls the virtual body model through motion to change the position to avoid the virtual distractor; and
  a VR motion functional quantitative analysis module configured to track and record somatosensory signals of the user to be trained at six degrees of freedom, and perform functional quantitative analysis based on the somatosensory signals at the six degrees of freedom to obtain functional quantitative results.

A computer device is proposed, including a memory and a processor, where the memory stores a computer program, and the computer program, when executed by the processor, causes the processor to perform the following steps: obtaining attribute information of a user to be trained, and determining a corresponding evaluation program based on the attribute information, where the attribute information includes a height, a weight, and a gender, and the evaluation program is used for selecting a plurality of short scenario items to play;
  during the playing, acquiring pupil change information and action information of the user in real time, determining a training scenario that the user is interested in based on the pupil change information, and determining a training solution based on the action information of the user;
  generating a virtual training scenario based on the training scenario that the user is interested in;
  obtaining a head position of the user to be trained, generating a virtual body model, and presenting the virtual body model in the virtual training scenario;

generating a virtual distractor in the virtual training scenario based on the training solution, where the user to be trained controls the virtual body model through motion to change the position to avoid the virtual distractor; and tracking and recording somatosensory signals of the user to be trained at six degrees of freedom, and performing functional quantitative analysis based on the somatosensory signals at the six degrees of freedom to obtain functional quantitative results.

A computer-readable storage medium storing a computer program, where the computer program, when executed by a processor, causes the processor to perform the following steps:

obtaining attribute information of a user to be trained, and determining a corresponding evaluation program based on the attribute information, where the attribute information includes a height, a weight, and a gender, and the evaluation program is used for selecting a plurality of short scenario items to play;

during the playing, acquiring pupil change information and action information of the user in real time, determining a training scenario that the user is interested in based on the pupil change information, and determining a training solution based on the action information of the user;

generating a virtual training scenario based on the training scenario that the user is interested in;

obtaining a head position of the user to be trained, generating a virtual body model, and presenting the virtual body model in the virtual training scenario;

generating a virtual distractor in the virtual training scenario based on the training solution, where the user to be trained controls the virtual body model through motion to change the position to avoid the virtual distractor; and tracking and recording somatosensory signals of the user to be trained at six degrees of freedom, and performing functional quantitative analysis based on the somatosensory signals at the six degrees of freedom to obtain functional quantitative results.

According to the VR rehabilitation training method with a quantitative evaluation function, the attribute information of the user to be trained is first obtained, and the corresponding evaluation program is determined based on the attribute information, where the evaluation program is used for selecting the plurality of short scenario items to play; during the playing, the pupil change information and the action information of the user am acquired in real time, the training scenario that the user is interested in is determined based on the pupil change information, and the training solution is determined based on the action information of the user; and the virtual training scenario is generated based on the training scenario that the user is interested in. The personalized virtual training scenario is provided for the user based on the point of interest of the user to be trained, which greatly contributes to improving the training effect. During the training, the somatosensory signals of the user to be trained at the six degrees of freedom are tracked and recorded and the functional quantitative analysis is performed to obtain the functional quantitative results, such that the quantitative evaluation function is provided for the VR rehabilitation training, thus contributing to more accurate training, and improving the training effect.

BRIEF DESCRIPTION OF DRAWINGS

To more clearly illustrate the technical solutions in the embodiments of the present disclosure or in the prior art, the accompanying drawings that need to be used in the description of the embodiments or the prior art will be briefly described below. Apparently, the accompanying drawings in the description below merely illustrate some embodiments of the present disclosure. Those of ordinary skill in the art may also derive other accompanying drawings from these accompanying drawings without creative efforts.

In the drawings.

DETAILED DESCRIPTION OF THE EMBODIMENTS

The technical solutions in the embodiments of the present disclosure will be clearly and completely described below in conjunction with the accompanying drawings in the embodiments of the present disclosure. Apparently, the described embodiments are merely some rather than all of the embodiments of the present disclosure. All other embodiments obtained by those of ordinary skill in the art based on the embodiments of the present disclosure without creative efforts should fall within the scope of protection of the present disclosure.

Figure 1:
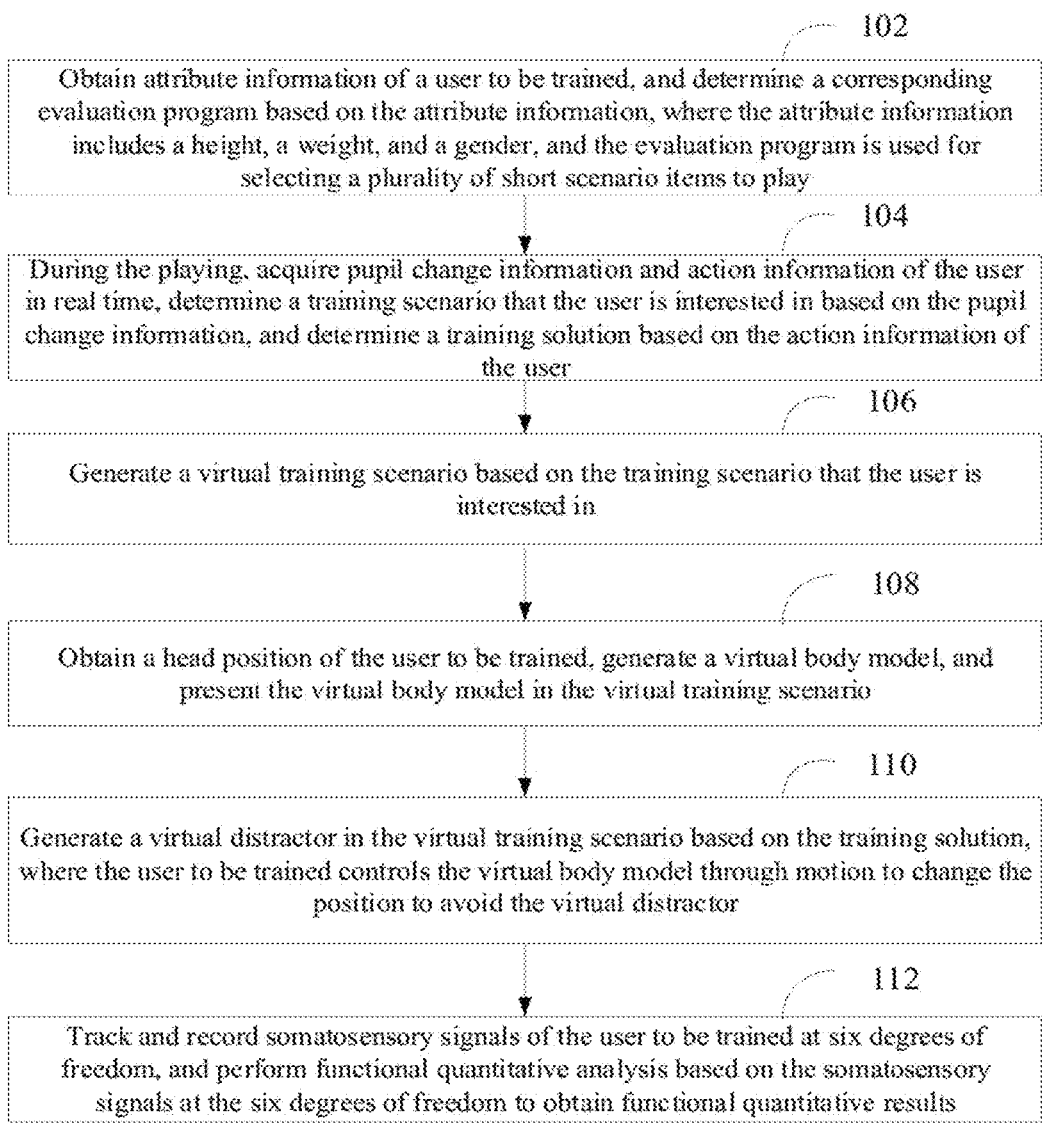
FIG. 1 is a flowchart of a VR rehabilitation training method with a quantitative evaluation function in one embodiment.

As shown in FIG. 1, in one embodiment, a VR rehabilitation training method with a quantitative evaluation function is proposed. The method includes the following steps.

In step 102, attribute information of a user to be trained is obtained, and a corresponding evaluation program is determined based on the attribute information, where the attribute information includes a height, a weight, and a gender, and the evaluation program is used for selecting a plurality of short scenario items to play.

First, the attribute information of the user can be obtained through direct input; and then, after the user to be trained wears a VR device, the corresponding evaluation program is started based on the attribute information, where the evaluation program is used for selecting the plurality of short scenario items to play. The evaluation program selects the plurality of short scenario items to play based on the attribute information. Different heights and weights have different requirements for sense of space, so scenarios with different senses of space are preset (for example, different ratios of image display are set) for the different heights and weights. The interest of different genders in scenarios often varies greatly, for example, girls prefer small fresh theme scenarios, while boys prefer war scenarios, etc. Therefore, the short scenarios that are more likely to be of interest by the user can be selected based on the different attribute information for item playing, which is conducive to quickly determining the point of interest of the user.

In step 104, during the playing, pupil change information and action information of the user are acquired in real time, a training scenario that the user is interested in is determined based on the pupil change information, and a training solution is determined based on the action information of the user.

In order to accurately determine the training scenario that the user is interested in, the pupil change information of the user is acquired in real time during the playing of the short scenarios, where the pupil change information includes a change in a pupil size and a change in a pupil movement trajectory. In one embodiment, in order to make recorded pupil changes more accurate, first, an initial pupil value of the user to be trained is determined, where the initial pupil value is a corresponding pupil value when the user is calm and does not observe anything yet; and then, the short scenarios are played, coordinates of pupils of the user to be trained at each time point and a pupil value at each time point are recorded, the change in the pupil movement trajectory (a change in horizontal movement) is obtained based on the coordinates of the pupils at each time point, and the change in the pupil size is obtained based on the change in the pupil value of the pupils.

A type of a virtual distractor capable of attracting the attention of the user can be obtained by comparing a time at which the virtual distractor occurs in each short scenario with the corresponding pupil change information; and then, the training scenario that the user is interested in can be obtained by comparing the pupil change information in each short scenario, the virtual training scenario corresponding to the user to be trained can be generated based on the determined type of the virtual distractor attracting the attention of the user and the training scenario that the user is interested in, which meets personalized features of the user and is beneficial for improving the training effect.

In step 106, a virtual training scenario is generated based on the training scenario that the user is interested in.

After the training scenario is determined, a VR head display main control terminal can generate the virtual training scenario based on the training scenario and present an image of the virtual training scenario in front of the user.

In step 108, a head position of the user to be trained is obtained, a virtual body model is generated, and the virtual body model is presented in the virtual training scenario.

A VR head display somatosensory recognition module can capture the head position of the trainee, generate the virtual body model, input it to the main control terminal, and then present the virtual body model in the determined virtual training scenario, where the virtual body model is presented in front of the user.

In step 110, a virtual distractor is generated in the virtual training scenario based on the training solution, where the user to be trained controls the virtual body model through motion to change the position to avoid the virtual distractor.

In order to train the user, a virtual distractor is generated in the virtual training scenario based on the determined training solution, and the user to be trained controls the virtual body model through a game to change the position to avoid the virtual distractor, so as to achieve the effect of rehabilitation exercise.

In step 112, somatosensory signals of the user to be trained at six degrees of freedom are tracked and recorded, and functional quantitative analysis is performed based on the somatosensory signals at the six degrees of freedom to obtain functional quantitative results.

In order to quantitatively evaluate the effect of rehabilitation exercise, in this application, the somatosensory signals of the user to be trained at the six degrees of freedom are tracked and recorded, and then a functional quantitative algorithm is performed based on the somatosensory signals to analyze trunk movement. In a head and neck region control training mode, forward flexion, backward extension, lateral flexion, and rotation of a neck are analyzed. In a sitting posture training mode, forward flexion, backward extension, lateral flexion, and rotation of a trunk are analyzed. In a standing posture training mode, forward flexion, backward extension, lateral bending, rotation, squatting, and stepping of the trunk are analyzed.

Figure 2:
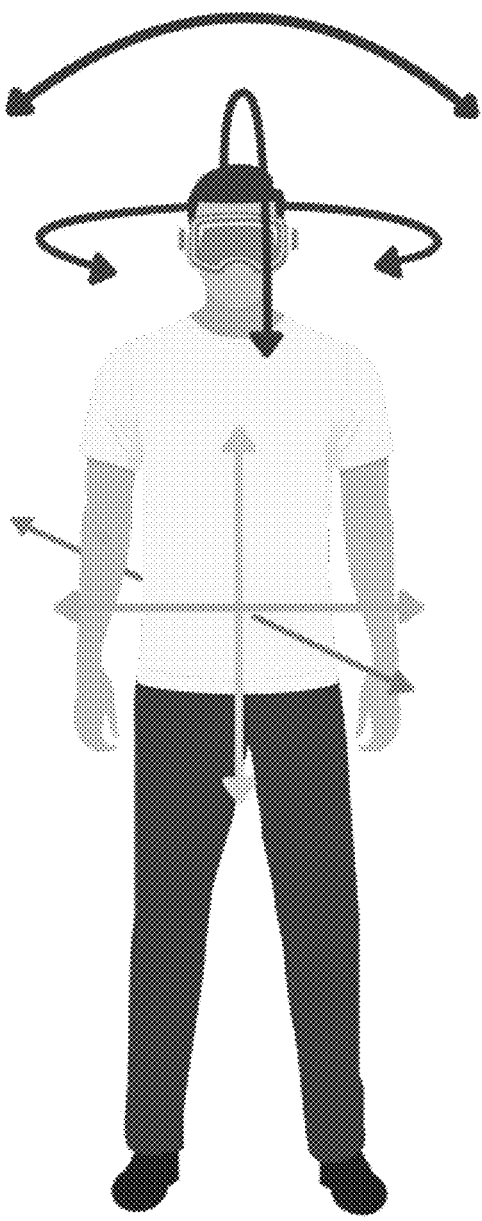
FIG. 2 is a schematic diagram of somatosensory recognition of six degrees of freedom in one embodiment.

The six degrees of freedom include degrees of freedom of movement along rectangular coordinate axes x, y, and z (corresponding to a front-back direction, a left-right direction, and an up-down direction) and degrees of freedom of rotation about the three coordinate axes. FIG. 2 is a schematic diagram of somatosensory recognition of six degrees of freedom. According to the present disclosure, positioning and free movement in a virtual reality space are implemented through VR head display technology and somatosensory recognition technology; rehabilitation training of trunk movement in different modes is implemented using motion interaction functions in different motion modes; functional quantitative evaluation of trunk movement is implemented through the functional quantitative algorithm; and a rehabilitation process of the trainee is digitally acquired to form a functional report updated in real time for a medical staff and a patient to know a rehabilitation status in real time.

According to the VR rehabilitation training method with a quantitative evaluation function, the attribute information of the user to be trained is first obtained, and the corresponding evaluation program is determined based on the attribute information, where the evaluation program is used for selecting the plurality of short scenario items to play; during the playing, the pupil change information and the action information of the user are acquired in real time, the training scenario that the user is interested in is determined based on the pupil change information, and the training solution is determined based on the action information of the user; and the virtual training scenario is generated based on the training scenario that the user is interested in. The personalized virtual training scenario is provided for the user based on the point of interest of the user to be trained, which greatly contributes to improving the training effect. During the training, the somatosensory signals of the user to be trained at the six degrees of freedom are tracked and recorded and the functional quantitative analysis is performed to obtain the functional quantitative results, such that the quantitative evaluation function is provided for the VR rehabilitation training, thus contributing to more accurate training, and improving the training effect.

In one embodiment, the determining a training scenario that the user is interested in based on the pupil change information includes: obtaining a tracked pupil change curve corresponding to each short scenario, where each short scenario contains a corresponding virtual distractor; determining a virtual distractor capable of attracting the attention of the user to be trained based on the virtual distractor occurring in each short scenario and the corresponding pupil change curve; and comparing the pupil change curve corresponding to each short scenario to determine the training scenario that the user is interested in.

The pupil change curve corresponding to each short scenario is extracted, an occurrence time and an occurrence position of the virtual distractor in each short scenario are extracted, the corresponding pupil change curve is extracted based on the occurrence time and the occurrence position of the virtual distractor, and the type of the virtual distractor that the user is interested in or that is most likely to attract the attention of the user is determined based on the pupil change curve. Then, the training scenario that the user is interested in, that is, the training scenario that the user is most interested in is determined by comparing the pupil change curves of the plurality of short scenarios.

In one embodiment, the method further includes: obtaining a rehabilitation item of the user, and determining a size, an occurrence position, and a speed of the virtual distractor in the training solution based on the rehabilitation item; and the method further includes: adjusting the training solution based on the functional quantitative results.

The rehabilitation item of the user represents a requirement and a difficulty of rehabilitation training of the user, so the size, the occurrence position, and the occurrence speed of the virtual distractor are determined based on the rehabilitation item. For example, for primary rehabilitation training, the distractor is generally a little big, the occurrence position is approximately a middle position, and the occurrence speed is a little low, such that the rehabilitation trainee can complete avoidance training. Conversely, as the training difficulty increases, the virtual distractor is a little small, there are more diverse occurrence positions, and the occurrence speed is higher. The training solution is determined based on specific training requirements, and then the difficulty of the training solution can be adjusted based on the functional quantitative results after the functional quantitative results are obtained.

In one embodiment, the tracking and recording somatosensory signals of the user to be trained at six degrees of freedom, and performing functional quantitative analysis based on the somatosensory signals at the six degrees of freedom to obtain functional quantitative results includes: obtaining a current training mode, and when the training mode is a head and neck region control training mode, extracting a somatosensory signal of a head and neck region, and analyzing forward flexion, backward extension, lateral flexion, and rotation of a neck based on the somatosensory signal of the head and neck region to obtain a functional quantitative result for each dimension; when the training mode is a sitting posture training mode, extracting a somatosensory signal of an upper body, and analyzing forward flexion, backward extension, lateral flexion, and rotation of a trunk based on the somatosensory signal of the upper body to obtain a functional quantitative result for each dimension; and when the training mode is a standing posture training mode, extracting a somatosensory signal of a whole body, and analyzing forward flexion, backward extension, lateral flexion, rotation, squatting, and stepping of the trunk based on the somatosensory signal of the whole body to obtain a functional quantitative result for each dimension.

Figure 3:
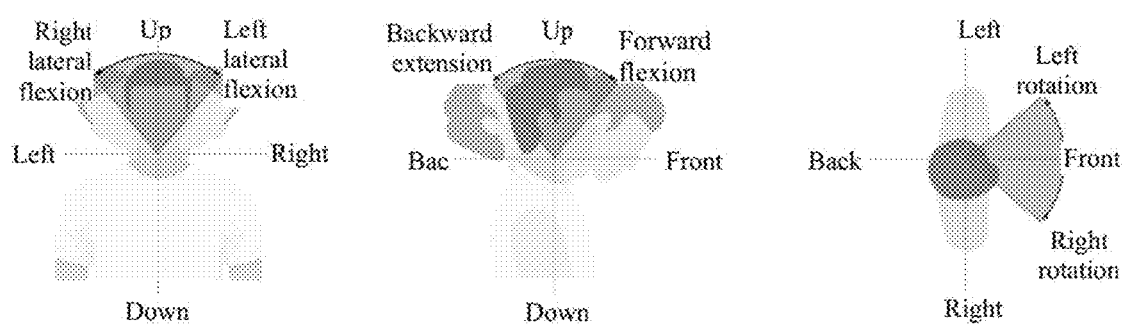
FIG. 3 is a schematic diagram of training in a head and neck region control training mode in one embodiment.
Figure 4:
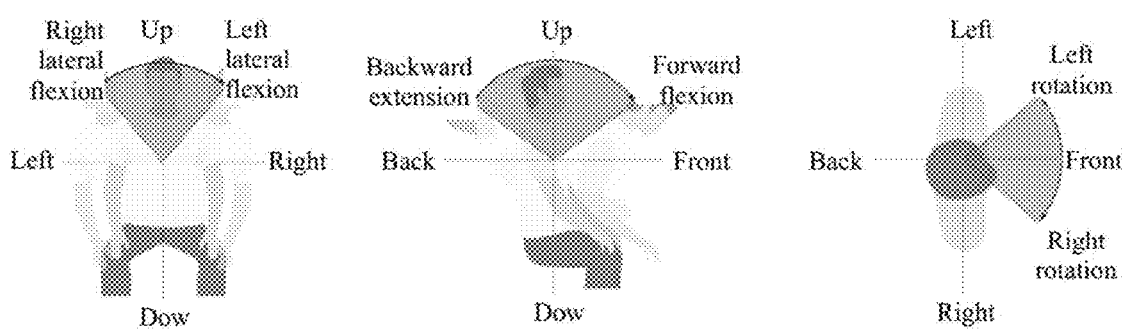
FIG. 4 is a schematic diagram of training in a sitting posture training mode in one embodiment.
Figure 5:
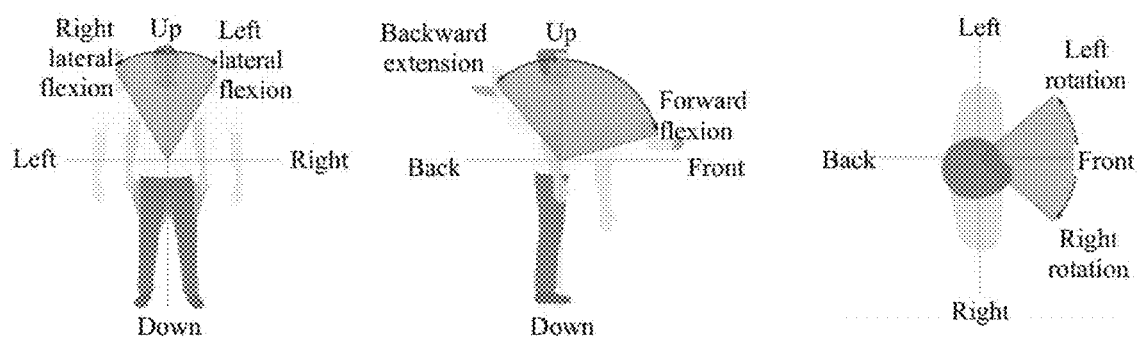
FIG. 5 is a schematic diagram of training in a standing posture training mode in one embodiment.

Three training modes can be set through a VR motion mode setting module, and refer to the head and neck region control training mode, the sitting posture training mode, and the standing posture training mode, respectively. In different training modes, the somatosensory signals are extracted with emphasis, thereby making the extracted somatosensory signals more accurate. FIG. 3 to FIG. 5 are schematic diagrams of training in a head and neck region control training mode, a sitting posture training mode, and a standing posture training mode.

In one embodiment, the analyzing forward flexion, backward extension, lateral flexion, and rotation of a neck based on the somatosensory signal of the head and neck region to obtain a functional quantitative result for each dimension includes: obtaining an avoidance action of avoiding the virtual distractor each time and an avoidance result, where each occurrence of the virtual distractor is corresponding to a corresponding functional training angle; and determining whether the functional training angle is met based on the avoidance action and the avoidance result, and obtaining the functional quantitative result.

In order to accurately quantity the functions of the user to be trained in various dimensions, double determination is performed based on the avoidance action and the avoidance result. The occurrence of the virtual distractor is corresponding to the corresponding functional training angle, that is, it is corresponding to a corresponding functional training task. Each occurrence of the virtual distractor is corresponding to a corresponding standard avoidance action. If the user responds slowly or incorrectly to cause that the avoidance action is inconsistent with the standard avoidance action, the avoidance is invalid, and the avoidance result does not need to be seen. Only when the avoidance action is consistent with the standard avoidance action, it continues to determine whether the avoidance is successful. When the avoidance is completely successful, it indicates that the corresponding functional training angle is met. When the avoidance is not completely successful, it indicates that the corresponding functional training angle is not met. Further, the situation that the avoidance is not completely successful may also be further refined, and functional quantitative scores are calculated based on the degree of avoidance.

In one embodiment, the determining whether the functional training angle is met based on the avoidance action and the avoidance result, and obtaining the functional quantitative result includes: determining whether the avoidance action is consistent with a preset action, when the avoidance action is consistent with the preset action, continuing to determine whether the virtual distractor is successfully avoided, and when the virtual distractor is successfully avoided, determining that the functional training angle is met, and obtaining the corresponding functional quantitative result based on the functional training angle.

In one embodiment, the determining a training solution based on the action information of the user includes: determining a training duration and a training difficulty based on a speed and range of the acquired actions of the user, and obtaining the training solution based on the training duration and the training difficulty.

In order to meet personalized requirements of the user, the training duration and the training difficulty in the training solution are determined based on the speed and range of the acquired actions of the user. In addition to the acquired action information, the rehabilitation item of the user may also be used to jointly develop the training solution, such that the training solution can be developed more accurately to improve the training effect.

Figure 6:
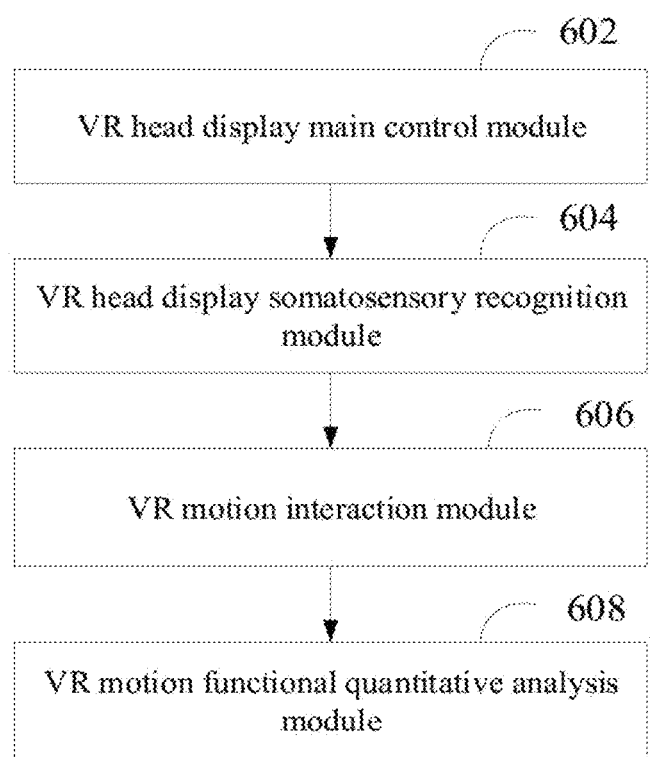
FIG. 6 is a structural block diagram of a VR rehabilitation training system with a quantitative evaluation function in one embodiment.

As shown in FIG. 6, in one embodiment, a VR rehabilitation training system with a quantitative evaluation function is proposed. The system includes:

a VR head display main control module 602 configured to: obtain attribute information of a user to be trained, and determine a corresponding evaluation program based on the attribute information, where the attribute information includes a height, a weight, and a gender, and the evaluation program is used for selecting a plurality of short scenario items to play; during the playing, acquire pupil change information and action information of the user in real time, determine a training scenario that the user is interested in based on the pupil change information, and determine a training solution based on the action information of the user;

and generate a virtual training scenario based on the training scenario that the user is interested in;

a VR head display somatosensory recognition module 604 configured to obtain a head position of the user to be trained, generate a virtual body model, and present the virtual body model in the virtual training scenario;

a VR motion interaction module 606 configured to generate a virtual distractor in the virtual training scenario based on the training solution, where the user to be trained controls the virtual body model through motion to change the position to avoid the virtual distractor; and a VR motion functional quantitative analysis module 608 configured to track and record somatosensory signals of the user to be trained at six degrees of freedom, and perform functional quantitative analysis based on the somatosensory signals at the six degrees of freedom to obtain functional quantitative results.

In one embodiment, the VR head display main control module 602 is further configured to: obtain a tracked pupil change curve corresponding to each short scenario, where each short scenario contains a corresponding virtual distractor; determine a virtual distractor capable of attracting the attention of the user to be trained based on a time point at which the virtual distractor occurs in each short scenario and the corresponding pupil change curve; and compare the pupil change curve corresponding to each short scenario to determine the training scenario that the user is interested in.

In one embodiment, the VR head display main control module 602 is further configured to obtain a rehabilitation item of the user, and determine a size, an occurrence position, and a speed of the virtual distractor in the training solution based on the rehabilitation item.

The system further includes an adjustment module configured to adjust the training solution based on the functional quantitative results.

In one embodiment, the VR motion functional quantitative analysis module 608 is further configured to obtain a current training mode, and when the training mode is a head and neck region control training mode, extract a somatosensory signal of a head and neck region, and analyze forward flexion, backward extension, lateral flexion, and rotation of a neck based on the somatosensory signal of the head and neck region to obtain a functional quantitative result for each dimension; when the training mode is a sitting posture training mode, extract a somatosensory signal of an upper body, and analyze forward flexion, backward extension, lateral flexion, and rotation of a trunk based on the somatosensory signal of the upper body to obtain a functional quantitative result for each dimension; and when the training mode is a standing posture training mode, extract a somatosensory signal of a whole body, and analyze forward flexion, backward extension, lateral flexion, rotation, squatting, and stepping of the trunk based on the somatosensory signal of the whole body to obtain a functional quantitative result for each dimension.

In one embodiment, the VR motion functional quantitative analysis module 608 is further configured to: obtain an avoidance action of avoiding the virtual distractor each time and an avoidance result, where each occurrence of the virtual distractor is corresponding to a corresponding functional training angle; and determine whether the functional training angle is met based on the avoidance action and the avoidance result, and obtain the functional quantitative result.

In one embodiment, the VR motion functional quantitative analysis module 608 is further configured to determine whether the avoidance action is consistent with a preset action, when the avoidance action is consistent with the preset action, continue to determine whether the virtual distractor is successfully avoided, and when the virtual distractor is successfully avoided, determine that the functional training angle is met, and obtain the corresponding functional quantitative result based on the functional training angle.

In one embodiment, the VR head display main control module 602 is further configured to determine a training duration and a training difficulty based on a speed and range of the acquired actions of the user, and obtain the training solution based on the training duration and the training difficulty.

Figure 7:
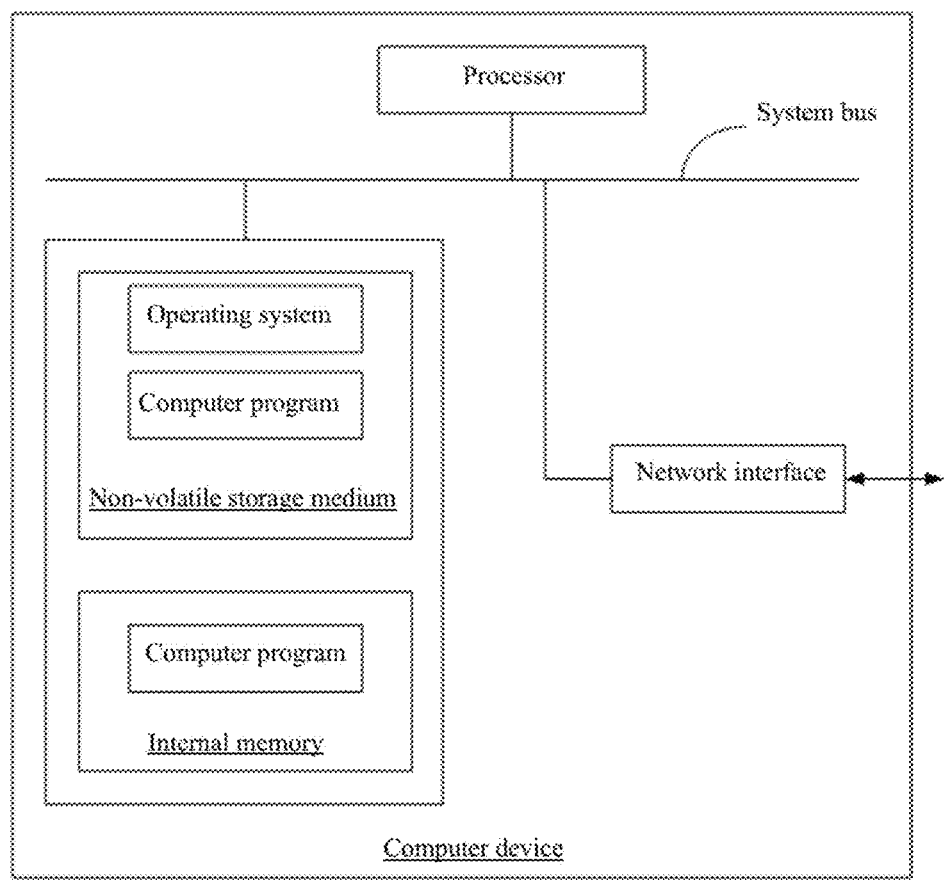
FIG. 7 is a schematic diagram of an internal structure of a computer device in one embodiment.

FIG. 7 shows a diagram of an internal structure of a computer device in one embodiment. The computer device may specifically be a terminal or a server. As shown in FIG. 7, the computer device includes a processor, a memory, and a network interface connected via a system bus. The memory includes a non-volatile storage medium and an internal memory. The non-volatile storage medium of the computer device stores an operating system and may also store a computer program, where the computer program, when executed by a processor, causes the processor to implement the VR rehabilitation training method with a quantitative evaluation function. The internal memory may also store a computer program, where the computer program, when executed by a processor, causes the processor to perform the VR rehabilitation training method with a quantitative evaluation function. Those skilled in the art can understand that the structure shown in FIG. 7 is only a block diagram of a partial structure related to the solution of this application and does not constitute a limitation to a device to which the solution of this application is applied. The specific device may include more or fewer components than shown in the figure, or combinations of some components, or have different component arrangements.

In one embodiment, a computer device is provided, including a memory and a processor, where the memory stores a computer program, and the computer program, when executed by the processor, causes the processor to perform steps of the VR rehabilitation training method with a quantitative evaluation function.

In one embodiment, a computer-readable storage medium is proposed, where a computer program is stored therein, and the computer program, when executed by a processor, causes the processor to perform steps of the VR rehabilitation training method with a quantitative evaluation function.

It can be understood that the VR rehabilitation training method and system with a quantitative evaluation function, the computer device, and the computer-readable storage medium belong to one general inventive concept, and the embodiments can be mutually applicable.

Those of ordinary skill in the art can understand that all or some of the processes in the method of the above embodiment may be implemented by a computer program instructing relevant hardware. The program may be stored in a non-volatile computer-readable storage medium, and when the program is executed, the processes of the above method embodiments may be included. Any reference to a memory, a storage, a database, or other media used in the various embodiments provided by this application may include a non-volatile and/or volatile memory. The non-volatile memory may include a read-only memory (ROM), a programmable ROM (PROM), an electrically programmable ROM (EPROM), an electrically erasable programmable ROM (EEPROM), or a flash memory. The volatile memory may include a random access memory (RAM) or an external cache memory. As an explanation rather than a limitation, the RAM is obtainable in various forms, such as a static RAM (SRAM), a dynamic RAM (DRAM), a synchronous DRAM (SDRAM), a dual data rate SDRAM (DDRS-DRAM), an enhanced SDRAM (ESDRAM), a synchlink DRAM (SLDRAM), a rambus direct RAM (RDRAM), a direct rambus dynamic RAM (DRDRAM), and a rambus dynamic RAM (RDRAM).

The technical features of the above embodiments may be combined arbitrarily. For the sake of brevity, all possible combinations of the technical features in the above embodiments are not described. However, the combinations of these technical features should be considered to be within the scope of this specification as long as there is no contradiction between them.

The above embodiments only express several implementations of this application and are described more specifically and detailedly, but should not be construed as limitations to the scope of the patent of this application. It should be pointed out that several modifications and improvements may also be made by those of ordinary skill in the art without departing from the conception of this application, and all fall within the scope of protection of this application. Therefore, the scope of patent protection of the present disclosure should be determined by the appended claims.

What is claimed is:

1. A virtual reality (VR) rehabilitation training method with a quantitative evaluation function, the method comprising:
    obtaining attribute information of a user to be trained, and determining a corresponding evaluation program based on the attribute information, wherein the attribute information comprises a height, a weight, and a gender, and the evaluation program is used for selecting a plurality of short scenario items to play;
    during the playing, acquiring pupil change information and action information of the user in real time, which comprises: arranging a front camera on a VR device and a mirror in front of the user, and acquiring actions of the user in the mirror by the front camera on the VR device; determining a training scenario that the user is interested in based on the pupil change information, which comprises: obtaining a tracked pupil change curve corresponding to each short scenario that contains a corresponding virtual distractor; determining a virtual distractor capable of attracting the attention of the user to be trained based on a time point at which the virtual distractor occurs in each short scenario and the corresponding pupil change curve; and comparing the pupil change curve corresponding to each short scenario to determine the training scenario that the user is interested in; determining a training solution based on the action information of the user, which comprises: determining a training duration and a training difficulty based on a speed and range of the acquired actions of the user; determining a type, a size, an occurrence position, and an occurrence speed of the virtual distractor based on the flexibility of the acquired limb actions of the user; and obtaining the training solution based on the training duration, the training difficulty and the type, the size, the occurrence position, and the occurrence speed of the virtual distractor;
    generating a virtual training scenario based on the training scenario that the user is interested in;
    obtaining a head position of the user to be trained, generating a virtual body model, and presenting the virtual body model in the virtual training scenario;
    generating a virtual distractor in the virtual training scenario based on the training solution, wherein the user to be trained controls the virtual body model through motion to change the position to avoid the virtual distractor; and
    tracking and recording somatosensory signals of the user to be trained at six degrees of freedom, and performing functional quantitative analysis based on the somatosensory signals at the six degrees of freedom to obtain functional quantitative results;
    the method further comprising:
    determining functional object conditions of the user to be trained based on the functional quantitative results, and determining limb actions that require enhanced training based on the functional object conditions; and
    adjusting the type, the size, the occurrence position, and the occurrence speed of the virtual distractor in the training solution based on the limb actions that require the enhanced training, to make the training solution better meet requirements of the user to be trained.

2. The method according to claim 1, further comprising: obtaining a rehabilitation item of the user, and determining the type, the size, the occurrence position, and the speed of the virtual distractor in the training solution based on the rehabilitation item.

3. The method according to claim 1, wherein the tracking and recording somatosensory signals of the user to be trained at six degrees of freedom, and performing functional quantitative analysis based on the somatosensory signals at the six degrees of freedom to obtain functional quantitative results comprises:
    obtaining a current training mode, and when the training mode is a head and neck region control training mode, extracting a somatosensory signal of a head and neck region, and analyzing forward flexion, backward extension, lateral flexion, and rotation of a neck based on the somatosensory signal of the head and neck region to obtain a functional quantitative result for each dimension;
    when the training mode is a sitting posture training mode, extracting a somatosensory signal of an upper body, and analyzing forward flexion, backward extension, lateral flexion, and rotation of a trunk based on the somatosensory signal of the upper body to obtain a functional quantitative result for each dimension; and
    when the training mode is a standing posture training mode, extracting a somatosensory signal of a whole body, and analyzing forward flexion, backward extension, lateral flexion, rotation, squatting, and stepping of the trunk based on the somatosensory signal of the whole body to obtain a functional quantitative result for each dimension.

4. The method according to claim 3, wherein the analyzing forward flexion, backward extension, lateral flexion, and rotation of a neck based on the somatosensory signal of the head and neck region to obtain a functional quantitative result for each dimension comprises:
    obtaining an avoidance action of avoiding the virtual distractor each time and an avoidance result, wherein each occurrence of the virtual distractor is corresponding to a corresponding functional training angle; and
    determining whether the functional training angle is met based on the avoidance action and the avoidance result, and obtaining the functional quantitative result.

5. The method according to claim 4, wherein the determining whether the functional training angle is met based on the avoidance action and the avoidance result, and obtaining the functional quantitative result comprises:

determining whether the avoidance action is consistent with a preset action, when the avoidance action is consistent with the preset action, continuing to determine whether the virtual distractor is successfully avoided, and when the virtual distractor is successfully avoided, determining that the functional training angle is met, and obtaining the corresponding functional quantitative result based on the functional training angle.

6. A computer device, comprising a memory and a processor, wherein the memory stores a computer program, and the computer program, when executed by the processor, causes the processor to perform steps of the VR rehabilitation training method with a quantitative evaluation function according to claim 1.

7. A VR rehabilitation training system with a quantitative evaluation function, the system comprising:

a VR head display main control module configured to: obtain attribute information of a user to be trained, and determine a corresponding evaluation program based on the attribute information, wherein the attribute information comprises a height, a weight, and a gender, and the evaluation program is used for selecting a plurality of short scenario items to play; during the playing, acquire pupil change information and action information of the user in real time, which comprises: arrange a front camera on a VR device and a mirror in front of the user, and acquire actions of the user in the mirror by the front camera on the VR device; determine a training scenario that the user is interested in based on the pupil change information, which comprises: obtain a tracked pupil change curve corresponding to each short scenario that contains a corresponding virtual distractor; determine a virtual distractor capable of attracting the attention of the user to be trained based on a time point at which the virtual distractor occurs in each short scenario and the corresponding pupil change curve; and compare the pupil change curve corresponding to each short scenario to determine the training scenario that the user is interested in; determine a training solution based on the action information of the user, which comprises: determine a training duration and a training difficulty based on a speed and range of the acquired actions of the user; determine a type, a size, an occurrence position, and an occurrence speed of the virtual distractor based on the flexibility of the acquired limb actions of the user; and obtain the training solution based on the training duration, the training difficulty and the type, the size, the occurrence position, and the occurrence speed of the virtual distractor; and generate a virtual training scenario based on the training scenario that the user is interested in;

a VR head display somatosensory recognition module configured to obtain a head position of the user to be trained, generate a virtual body model, and present the virtual body model in the virtual training scenario;

a VR motion interaction module configured to generate a virtual distractor in the virtual training scenario based on the training solution, wherein the user to be trained controls the virtual body model through motion to change the position to avoid the virtual distractor;

a VR motion functional quantitative analysis module configured to track and record somatosensory signals of the user to be trained at six degrees of freedom, and perform functional quantitative analysis based on the somatosensory signals at the six degrees of freedom to obtain functional quantitative results; and an adjustment module configured to determine functional object conditions of the user to be trained based on the functional quantitative results, determine limb actions that require enhanced training based on the functional object conditions, and adjust the type, the size, the occurrence position, and the occurrence speed of the virtual distractor in the training solution based on the limb actions that require the enhanced training, to make the training solution better meet requirements of the user to be trained.

\* \* \* \* \*